US012687260B2

(12) United States Patent
Showers et al.

(10) Patent No.: US 12,687,260 B2
(45) Date of Patent: *Jul. 21, 2026

(54) CONTROLLED DOSING OF LIQUID CRYOGEN

(71) Applicant: Vacuum Barrier Corporation, Woburn, MA (US)

(72) Inventors: Erik Robert Showers, Boxford, MA (US); John Walker Ross, Ipswich, MA (US); David Tucker, Groveland, MA (US)

(73) Assignee: Vacuum Barrier Corporation, Woburn, MA (US)

( * ) Notice: Subject to any disclaimer, the term of this patent is extended or adjusted under 35 U.S.C. 154(b) by 110 days.

This patent is subject to a terminal disclaimer.

(21) Appl. No.: 18/678,412

(22) Filed: May 30, 2024

(65) Prior Publication Data

US 2025/0237357 A1 Jul. 24, 2025

Related U.S. Application Data

(63) Continuation of application No. 18/425,621, filed on Jan. 29, 2024, now Pat. No. 12,031,680.

(Continued)

(51) Int. Cl.
*F17C 13/04* (2006.01)
*A61L 2/24* (2006.01)
(Continued)

(52) U.S. Cl.
CPC .............. *F17C 13/04* (2013.01); *A61L 2/24* (2013.01); *A61L 2/26* (2013.01); *B65B 31/006* (2013.01);
(Continued)

(58) Field of Classification Search
CPC .............. F17C 13/04; F17C 2205/0326; F17C 2221/014; F17C 2223/0161;
(Continued)

(56) References Cited

U.S. PATENT DOCUMENTS 3,794,039 A 2/1974 Kollner et al.
3,972,202 A 8/1976 Stearns
(Continued)

FOREIGN PATENT DOCUMENTS

EP 1762538 A1 3/2007
GB 2169998 A 7/1986
(Continued)

OTHER PUBLICATIONS

International Search Report and Written Opinion in International Appln. No. PCT/US2024/34302, mailed on Oct. 25, 2024, 13 pages.
(Continued)

*Primary Examiner* — Frederick C Nicolas
(74) *Attorney, Agent, or Firm* — Fish & Richardson P.C.

(57) ABSTRACT

An aseptic liquid cryogen dosing head has a liquid cryogen reservoir in communication with a dosing outlet. An electromagnetic actuator is attached to an upper end of a dosing valve stem and is operable to move the dosing valve stem to open and close the dosing outlet. An air-tight seal extends about the dosing valve stem and separates the liquid cryogen reservoir from a cavity between the seal and the electromagnetic actuator. A controller is operable to perform a head leakage test, including pressurizing the cavity with a pressure higher than a pressure within the reservoir, to check for leakage past the seal; and pressurizing the reservoir to check for leakage from the liquid cryogen reservoir.

15 Claims, 4 Drawing Sheets

Related U.S. Application Data

(60) Provisional application No. 63/623,393, filed on Jan. 22, 2024.

(51) Int. Cl.

| | |
|---|---|
| *A61L 2/26* | (2006.01) |
| *B65B 3/04* | (2006.01) |
| *B65B 31/00* | (2006.01) |
| *B65B 55/00* | (2006.01) |
| *B67C 3/00* | (2006.01) |
| *B67C 3/22* | (2006.01) |
| *B67C 3/26* | (2006.01) |

(52) U.S. Cl.
CPC .............. *B67C 3/005* (2013.01); *B67C 3/007* (2013.01); *B67C 3/222* (2013.01); *B67C 3/26* (2013.01); *A61L 2202/14* (2013.01); *B67C 2003/228* (2013.01); *F17C 2205/0326* (2013.01); *F17C 2221/014* (2013.01); *F17C 2223/0161* (2013.01); *F17C 2260/038* (2013.01); *F17C 2270/059* (2013.01)

(58) Field of Classification Search
CPC ......... F17C 2260/038; F17C 2270/059; B67C 3/005; B67C 3/26; B67C 3/007; B67C 3/222; B67C 2003/228; A61L 2/24; A61L 2/26; A61L 2202/14; B65B 31/006
See application file for complete search history.

(56) References Cited

U.S. PATENT DOCUMENTS

| | | | |
|---|---|---|---|
| 4,349,358 | A | 9/1982 | Tarancon |
| 4,715,187 | A | 12/1987 | Stearns |
| 4,796,434 | A | 1/1989 | Garnreiter |
| 4,848,093 | A | 7/1989 | Simmonds et al. |
| 4,854,128 | A | 8/1989 | Zeamer |
| 4,865,088 | A | 9/1989 | Stearns |
| 4,899,546 | A | 2/1990 | Eigenbrod |
| 5,131,440 | A | 7/1992 | Quinn |
| 5,169,031 | A | 12/1992 | Miller |
| 5,353,849 | A | 10/1994 | Sutton et al. |
| 5,400,601 | A | 3/1995 | Germain et al. |
| 5,533,341 | A | 7/1996 | Schvester et al. |
| 5,562,132 | A | 10/1996 | Siegele et al. |
| 5,711,354 | A | 1/1998 | Siegele et al. |
| 5,743,096 | A | 4/1998 | Blanton et al. |
| 5,749,232 | A | 5/1998 | Sauer |
| 5,771,697 | A | 6/1998 | Germain et al. |
| 5,865,225 | A * | 2/1999 | Weiss ...................... B67C 3/204 141/145 |
| 5,988,206 | A | 11/1999 | Bare et al. |
| 6,047,553 | A | 4/2000 | Germain |
| 6,098,674 | A | 8/2000 | Germain et al. |
| 7,281,550 | B2 | 10/2007 | Ziegler |
| 7,571,749 | B2 * | 8/2009 | Stocchi ................... B67C 3/04 141/105 |
| 12,031,680 | B1 | 7/2024 | Showers et al. |
| 2005/0011580 | A1 | 1/2005 | Ziegler |
| 2008/0256902 | A1 | 10/2008 | Lorcks et al. |
| 2017/0158481 | A1 | 6/2017 | Clusserath et al. |

FOREIGN PATENT DOCUMENTS

| | | |
|---|---|---|
| JP | H06-13920 B2 | 2/1994 |
| JP | H1143111 A | 2/1999 |
| WO | WO 2023/286802 A1 | 1/2023 |

OTHER PUBLICATIONS

Extended European Search Report in European Appln. No. 24754209.5, mailed on Nov. 26, 2025, 12 pages.
Extended European Search Report in European Appln. No. 25197035.6, mailed on Dec. 1, 2025, 12 pages.

* cited by examiner

CONTROLLED DOSING OF LIQUID CRYOGEN

CLAIM OF PRIORITY

This application is a continuation of U.S. patent application Ser. No. 18/425,621, filed on Jan. 29, 2024, which claims priority under 35 USC § 119 (e) to U.S. Patent Application Ser. No. 63/623,393, filed on Jan. 22, 2024, the entire contents of which are hereby incorporated by reference.

TECHNICAL FIELD

This invention relates to systems and methods for delivering controlled doses of a liquid cryogen, such as liquid nitrogen.

BACKGROUND

In some processes, it is important to deliver a known amount of a cryogenic liquid. For example, doses of liquid nitrogen are delivered to containers that are then capped immediately in a beverage packaging line so that nitrogen vaporizing after capping pressurizes the container. In that process, the amount of liquid delivered must be carefully controlled. If too little liquid cryogen is administered, the container may collapse when it experiences significant forces. If too much liquid cryogen is delivered, excessive pressure builds up in the container causing it to deform or rupture. Even when liquid cryogen (usually nitrogen) is provided as a source of inert gas in the container and not to pressurize it, cryogen delivery must be reliable and consistent without gaps or surges of liquid.

Controlling the amount or dose of liquid nitrogen delivered can be difficult, particularly if the doses must be rapidly administered as is the case for a high speed canning or bottling assembly line. The large change in density resulting from vaporization of liquid means that devices dispensing a predetermined volume of fluid, such as valves, will not provide consistent amounts of cryogen unless the vapor/liquid state of the fluid is controlled.

Providing controlled doses of liquid cryogen under aseptic conditions involves other considerations, such as how to ensure that the dosing equipment and the cryogen itself is reasonably free of contamination or sterile. Sterilization of dosing equipment can be challenging.

SUMMARY

According to one aspect of the invention, an aseptic liquid cryogen dosing head has a liquid cryogen reservoir in communication with a dosing outlet, a dosing valve stem extending through the liquid cryogen reservoir and having a lower, distal end configured to selectively open and close the dosing outlet, and an electromagnetic actuator attached to an upper end of the dosing valve stem and operable to move the dosing valve stem to open and close the dosing outlet.

In some embodiments, the dosing head also includes a seal extending about the dosing valve stem and separating the liquid cryogen reservoir from a cavity between the seal and the electromagnetic actuator. The seal provides an air-tight seal during operation.

In many examples, the head includes a controller, which may be positioned some distance from the head but is nevertheless operable to perform a head leakage test, including pressurizing the cavity with a pressure higher than a pressure within the reservoir, to check for leakage past the seal, and pressurizing the reservoir to check for leakage from the liquid cryogen reservoir.

In some cases, the controller is also operable to sterilize the head, by a processing including introducing a pressurized sterilization fluid into the reservoir, while introducing a gas at a countering pressure into the cavity, thereby keeping the dosing outlet in a closed condition during sterilization.

In some cases, the controller sequences valves to sterilize the head, and introduces a pressurized fluid into the reservoir, while simultaneously counter pressurizing the non-aseptic cavity of the dosing head, thereby keeping the dosing outlet in a closed condition during sterilization.

The pressurized sterilization fluid may be, for example, steam.

In some cases the controller is configured to perform the head leakage test both before and after sterilizing the head.

In some embodiments, the seal comprises a diaphragm secured to the dosing valve stem. In some examples, the dosing valve stem has both a lower valve stem portion disposed below the diaphragm, and an upper valve stem portion disposed above the diaphragm and connected to the lower valve stem portion by a threaded connection.

In some embodiments, the reservoir includes a tube extending from above a liquid cryogen level to below the liquid cryogen level and surrounding the dosing valve stem.

In some cases, the liquid cryogen reservoir is contained within a housing connecting the dosing outlet with the electromagnetic actuator. The housing and the dosing valve stem are preferably fashioned primarily of materials with coefficients of thermal expansion that differ by less than one percent. In some examples, both the housing and the dosing valve stem are fashioned of stainless steel.

In some embodiments, the reservoir comprises a liquid cryogen feed conduit filled with liquid cryogen in operation and extending from a primary cavity of the reservoir to the dosing outlet.

In some examples, the electromagnetic actuator is a servomotor. For example, the servomotor may include an encoder that provides valve stem position feedback to the controller.

In some cases, the electromagnetic actuator is controllable to alter a dosing valve stem displacement distance and duration. Such control may be accomplished by altering target displacement and timing values of the actuator control signal. The electromagnetic actuator may also be controllable to alter a rest position of the dosing valve stem with respect to the dosing outlet, such as by changing a null position of the valve stem displacement control.

Some embodiments also have a dosing outlet gas flow valve controllable to introduce a flow of sterile gas from a pressurized source to the dosing outlet to inhibit frost accumulation. The dosing outlet gas flow valve may be controllable to open when the electromagnetic actuator is not operating to dispense a dose of liquid cryogen, for example. The dosing outlet gas flow valve may include a fixed bypass orifice that allows a continuous flow of the sterile gas to the dosing outlet when the electromagnetic actuator is operating to dispense a dose of liquid cryogen, and may be arranged to introduce the flow of the sterile gas to a portion of the dosing outlet open to atmospheric pressure.

In some cases, the lower, distal end of the dosing valve stem has a thermoplastic cap that engages a seat of the dosing outlet.

Another aspect of the invention features a method of sterilizing a liquid cryogen dosing head, the method including performing a system leakage test by pressurizing a first cavity between a dosing valve stem seal and an electromagnetic dosing actuator, as well as a second cavity on an opposite side of the dosing valve stem seal, to check for system leakage, then testing for leakage past the seal by reducing pressure in the second cavity and, with the second cavity pressure reduced, monitoring pressure in the first cavity over a predetermined time interval. In response to passing the seal leakage test, a sterilization fluid is introduced to the second cavity and maintained in the second cavity under conditions that cause sterilization of the second cavity and a dosing valve stem extending from the dosing valve stem seal to a liquid cryogen dosing outlet, while maintaining sufficient pressure in the first cavity to keep the dosing valve stem seated at the liquid cryogen dosing outlet.

In some cases, the seal leakage test and second cavity leakage test are both performed before and after introducing and maintaining the sterilization fluid in the second cavity.

At least many embodiments of the invention can provide a particularly high aseptic dosing speed. This can be accomplished, at least in part, by enabling the use of a high speed electromagnetic actuator under conditions that protect the actuator during sterilization.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
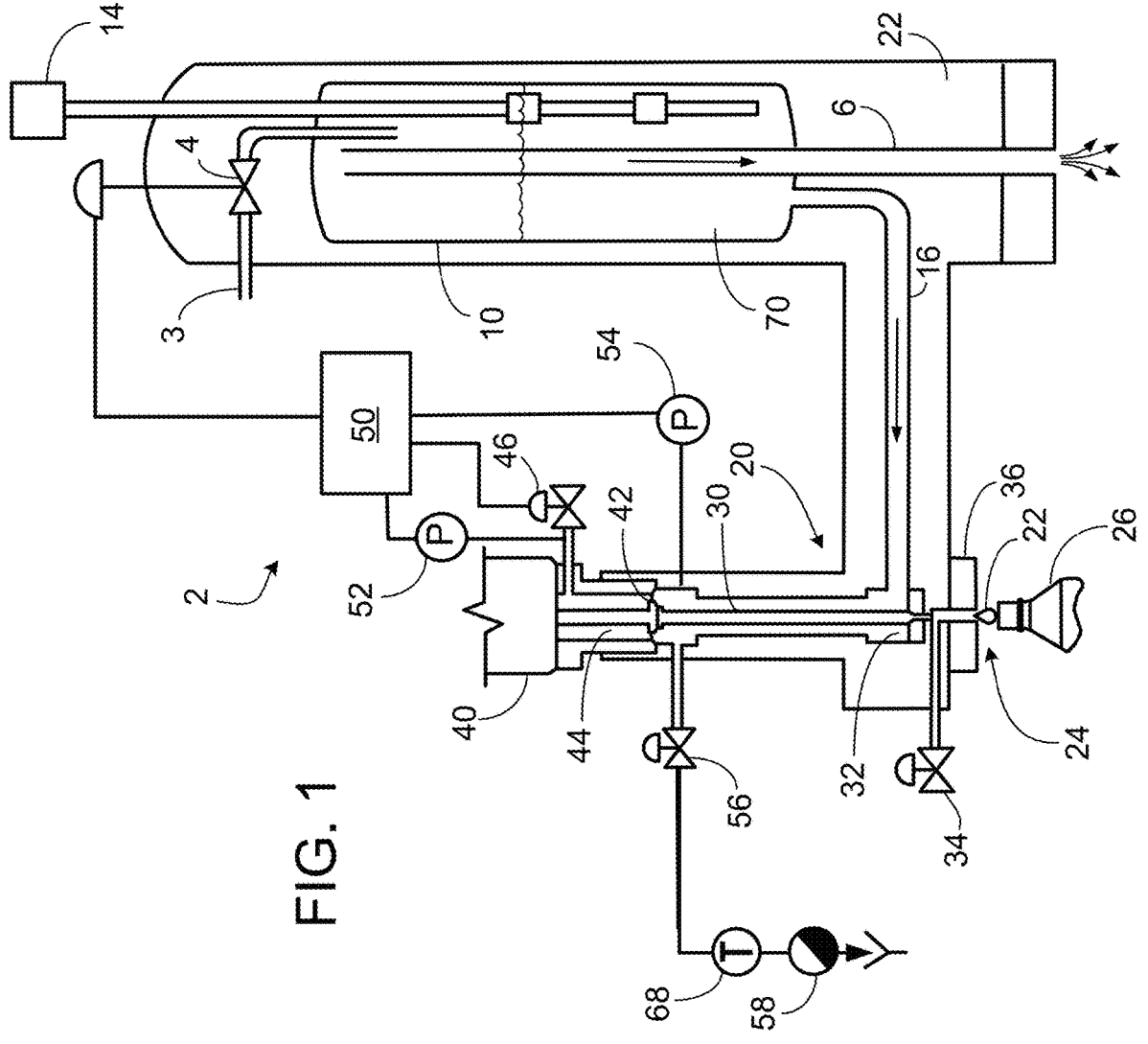
FIG. 1 is a schematic diagram of a first embodiment of a liquid cryogen delivery system for controlled dosing of liquid cryogen.

Referring first to FIG. 1, in aseptic liquid cryogen dosing head 2, cryogen is supplied from a pressurized source and travels through vacuum jacketed piping 3 through a controllable inlet valve 4 into a phase separating reservoir 10. Fill valve 4 can be controlled to ensure that the incoming cryogen substantially liquefies. A sterile filter is located in the piping 3 before inlet valve 4, which prevents unwanted particles from entering the reservoir. As the two-phase cryogen mixture flows into the reservoir 10, the gas phase is vented to atmosphere through vent conduit 6. The liquid phase collects in reservoir 10 and is maintained at a constant level by controlling valve 4 in response to a level sensor 14. Liquid flows freely by gravity down the feed conduit 16, which is an extension of reservoir 10, to a dosing valve 20. The pressure head at the lower end of the dosing valve is controlled by controlling the level of liquid cryogen in the reservoir. The entire reservoir, including feed conduit 16, is encased within a vacuum insulation chamber 22 to minimize heating.

Dosing valve 20 is controlled to dispense discrete doses 22 of liquid cryogen, such as liquid nitrogen, from the dosing outlet 24 arranged such that each dispensed dose 22 falls into a container 26 passing under the outlet. Valve 20 may be controllably cycled at a high rate, to dispense discrete doses 22 at a rate of up to, for example, 2,000 doses per minute, each dose falling into a respective container. Each dose may be, for example, between 0.01 and 1.0 ml of liquid cryogen. Each container moves to a capping station immediately after dosing.

Dosing valve 20 has a valve stem 30 that cycles vertically to seat and unseat against a valve seat 32 at the dosing outlet, thereby closing and opening the outlet. The stem is stainless steel with a tip of thermoplastic to provide a sealing surface. When the outlet is open, liquid cryogen is forced through the outlet by static pressure within the reservoir, as determined by the level of liquid. The valve seat is a surface of the outlet nozzle, which may define a fixed output orifice of, for example, 0.065 inch diameter (in some cases between 0.015 and 0.12 inch diameter). Valve stem 30 is cycled by an electromagnetic linear actuator 40 that pushes and pulls on the valve stem in response to controlled electromagnetic force. A diaphragm 42 forms a seal that extends about the dosing valve stem and separates the liquid cryogen reservoir from a cavity 44 between the diaphragm and the electromagnetic actuator 40. The diaphragm provides an air-tight annular seal, with an inner portion of the diaphragm secured to the valve stem and an outer portion of the seal secured to the surrounding structure, such as by being captured at the inner end of a fitting that mounts the actuator. In this example the valve stem has an upper section secured to the actuator, and a lower section extending to the valve seat. The two sections are threaded together at the diaphragm. The diaphragm flexes during each actuation cycle of the valve stem, allowing the stem to move a vertical distance of up to about 0.1 inch (2.5 mm) for a full stroke. Diaphragm 42 can be of EPDM molded over a fabric core, for example. In operation, actuator 40 can be controlled to modulate the amount of lift of the valve stem, and to alter the open and close rate of the dosing outlet, thereby changing the dosage volume and dispensing parameters to as needed for optimum dosing. Control of the dosing volume can be, for example, a function of a sensed container pressure downstream of the capping station. Changing the dosing parameters by control of the linear actuator avoids the need to shut down the line to change orifice sizes.

Linear actuator 40, in this example, is a linear servomotor (electric cylinder) with a built-in encoder having a resolution of 5 $\mu$m, an operating voltage of 48 VDC, a maximum stroke of 10 mm, and a peak output force of 100 N. Suitable actuators are available commercially. Such an actuator is precisely controlled by pulse-width modulation.

A dosing outlet gas flow valve 34 is controllable to introduce a flow of dry sterile gas from a pressurized source (not shown) to the dosing outlet to help inhibit frost accumulation at the dosing outlet. The dosing outlet gas flow valve is preferably controlled to open when the electromagnetic actuator is not operating to dispense a dose of liquid cryogen, and to close during dosing. Dosing outlet gas flow valve 34 includes a fixed bypass orifice that allows a continuous flow of the sterile gas to the dosing outlet when the electromagnetic actuator is operating to dispense a dose of liquid cryogen. In this manner, a small flow of sterile gas is always flowing out of the outlet to keep the outlet clean and frost-free, and a high flow of sterile gas flows during periods of non-dosing. As illustrated, the dosing outlet gas flow valve is arranged to introduce the flow of the sterile gas to a portion of the dosing outlet open to atmospheric pressure. A heated containment plate 36 at the outlet works in combination with the purge gas from valve 34 to maintain warm, ice free surfaces during liquid cryogen dosing.

Aseptic dosing requires that the dosing system be periodically sterilized. Such sterilization typically involves introducing high temperature (e.g., 250° F.) steam to all internal surfaces that are normally exposed to the cryogen (either liquid or gas) downstream of the fill valve, at a pressure of about 30 psi, and maintaining such temperatures and pressures a sufficient time to kill any bacteria or pathogens on the surfaces. A sterilization cycle is described below. In order to protect diaphragm 42 during sterilization, a non-aseptic gas is introduced to cavity 44 by control of backpressure valve 46, thereby balancing at least most of the steam pressure in the reservoir to keep the valve stem from unseating from the valve seat until desired. In pneumatic systems the pneumatic dosing valve actuator will generally be able to develop sufficient downward force to keep the valve seated during sterilization. Pressurizing cavity 44 allows the use of electromagnetic actuators that do not generally provide sufficient axial force to balance steam pressures.

Prior to performing a sterilization cycle, the integrity of diaphragm 42 must be tested. Otherwise, high temperature steam may damage the linear actuator. To test the integrity of the diaphragm, cavity 44 may be pressurized to a test pressure above any pressure in the reservoir, and the cavity pressure monitored over a predetermined time interval to confirm that any leakage past the diaphragm is insignificant. This diaphragm testing can be part of an overall head leakage test in which both cavity 44 and the reservoir are pressurized to check for leakage through any part of the aseptic system, and then pressure in the reservoir is released while pressure is held in cavity 44 to perform the diaphragm integrity test.

Aseptic dosing also requires that the mechanical components of the system withstand extreme temperature changes, such as from –320° F. liquid nitrogen temperatures during operation, to +250° F. steam temperatures during sterilization. Such high temperature changes can cause significant issues due to thermal expansion. Given that the dosing valve stem can be up to 30 inches long in an aseptic system, care must be taken to avoid problems due to changes in overall length of the valve stem due to thermal expansion. For example, the structure connecting the dosing outlet to the linear actuator should be of materials with an overall net coefficient of expansion identical to, or substantially identical to, that of the valve stem. Preferably, the housing and the dosing valve stem are fashioned primarily of materials with coefficients of thermal expansion that differ by less than one percent. In this example such structure is also made of stainless steel. Additionally, a homing signal can be sent to the linear actuator after the valve stem has been submerged in liquid cryogen for a period of time.

A controller 50 controls the various valves to perform pressure tests and to run a sterilization cycle. This may be the same controller that controls the linear actuator during operation. At the beginning of a diaphragm pressure test, the controller opens backpressure valve 46 until pressure in cavity 44, as measured by cavity pressure sensor 52, exceeds the pressure in reservoir 10 below the diaphragm, as measured by valve pressure sensor 54, by a fixed amount, such as 10 psi. Valve 46 is closed and the cavity pressure monitored for a fixed time interval, such as two minutes. If the cavity pressure drops by more than a predetermined amount, such as 3 psi, over the time interval, the controller sends an alert that the diaphragm pressure test failed, and the system is serviced.

Once the diaphragm test is complete, controller 50 can also run a full system leak test. With the steam trap exit valve 56 closed, the valve stem seated and the reservoir vent conduit 6 closed (by a vent valve, not shown), controller pressurizes both reservoir 10 and cavity 44 by controlling valves 4 and 46 until pressures at sensors 52 and 54 are both within a predetermined pressure window. Valves 4 and 46 are then closed and the pressure at sensor 54 is monitored over a set time interval. If the reservoir pressure drops by more than a predetermined amount, such as 3 psi, over the time interval, the controller sends an alert that the system leakage test failed, and the system is serviced. The diaphragm pressure test, and the system leakage test, are normally both performed before and after system sterilization.

Figure 3:
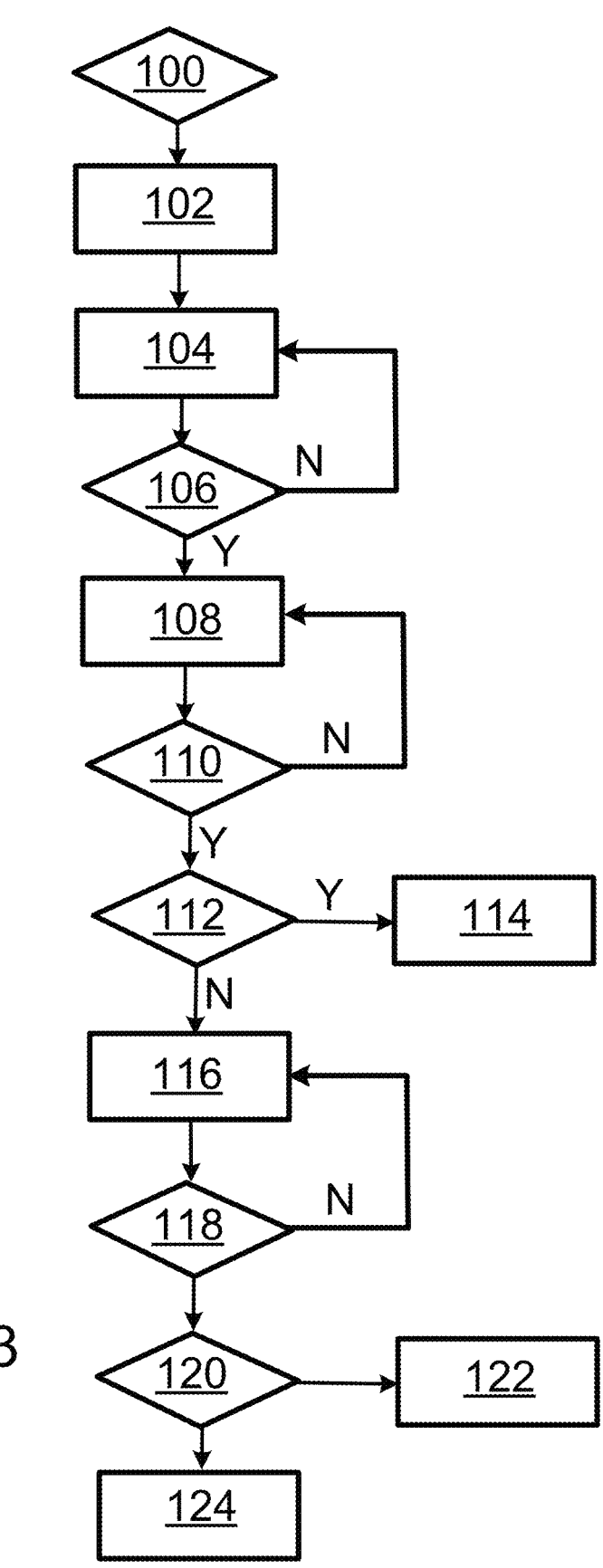
FIG. 3 is a flow diagram of a pressure test sequence.

This sequence of these two tests is illustrated in the flow diagram of FIG. 3. Upon initiation 100 of the pressure test sequence, controller first closes any open valves 102, then opens 104 back pressure valve 46 and the inlet valve and starts a 30 second timer 106 while the main reservoir is pressurized in parallel with cavity 44. When the timer has reached 30 seconds, back pressure valve 46 and inlet valve 4 are closed 108 and a two minute timer 110 is started. At the conclusion of two minutes, reservoir pressure is checked 112 at pressure sensor 54. If the pressure has dropped more than 3.0 psi during the two minutes, a signal is sent 114 indicating a failure of the pressure test. Otherwise, valves 56 and 64 are opened 116 to depressurize the reservoir, leaving cavity 44 under pressure, and a third timer 118 is started. At the conclusion of two minutes, pressure in cavity 44 is checked 120 and if cavity pressure has dropped below a predetermined setpoint, a signal is sent 122 indicating a failure of the diaphragm integrity test. Otherwise, the pressure test successfully concludes 124.

For system sterilization, controller 50 controls inlet valve 4, through which pressurized steam (or other sterilizing media) is introduced to the reservoir to sterilize the system, and exit valve 56, through which the steam is cleared through a steam trap 58 following sterilization. As noted above, the controller simultaneously pressurizes cavity 44 with inert gas during sterilization, by controlling valve 46, to help to balance loads on the diaphragm and keep the valve stem seated. The reservoir vent valve (not shown) is also kept closed during sterilization. Exit valve 56 may remain at least partially open during filling of the reservoir with steam, to ensure a flow of sterilizing steam into the dosing valve and up to the diaphragm. The controller can monitor temperature at various points in the system to confirm that sterilization temperatures and times were achieved before venting through the exit valve. Sterilization of the dosing outlet can be performed by lifting the valve stem under steam conditions and allowing pressurized steam to vent through the outlet.

Figure 4:
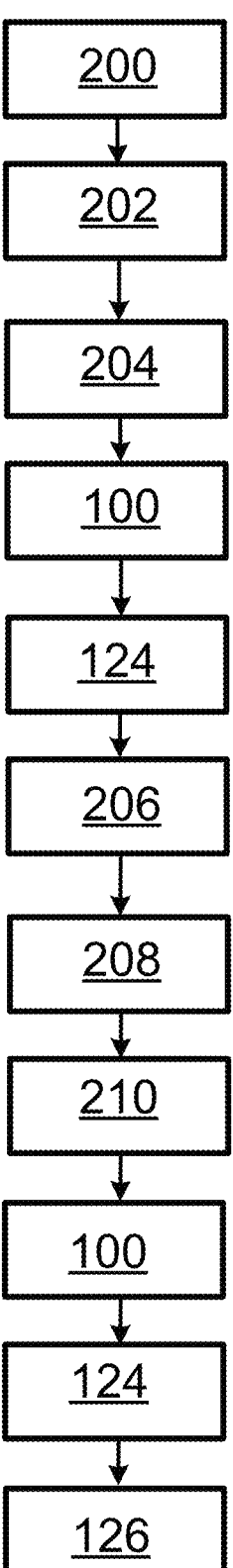
FIG. 4 is a flow diagram of a sterilization procedure including pressure test sequences.

The sterilization sequence is shown schematically in FIG. 4. Upon initiation 200, such as at the conclusion of a dosing run, the system is drained 202 of cryogen by opening dosing outlet 24 with the fill valve 4 closed, and maintaining this configuration until level sensor 14 indicates an empty reservoir for a predetermined period of time, such as 5 minutes. Next, fill valve 4 is opened to a flow of dry gas and the reservoir is heated 204 to a temperature above negative 100° F. Once elevated reservoir temperature is confirmed, the pressure testing discussed above is initiated 100. At the successful conclusion 124 of the pressure testing, valve 4 is opened 206 to a flow of heated sterilization fluid, such as steam. The various valves leading from the reservoir are cycled to ensure that the entire reservoir is sufficiently exposed to the heated steam, while cavity 44 is pressurized via valve 46 sufficiently to prevent a high pressure differential across diaphragm 42. During this sterilization step, the dosing outlet 24 may be cleaned, either by introducing a sterilization fluid through valve 34 or by sterilizing the outlet from below. Reservoir temperature is monitored until such temperature has exceeded a predetermined threshold, such as 250° F., for a minimum period of time, such as 30 minutes, to ensure sterilization of all interior surfaces. Following sterilization, the sterilization fluid is purged 210 from the system using a dry flow of sterile gas through inlet valve 4, cycling the other valves in the system as needed to ensure that the entire system is purged. Following purging, the pressure test sequence is again initiated 100 to confirm that the system is sealed and ready for further dosing. A dry gas flow is also provided through the dosing outlet valve 34. Once the pressure tests are successfully completed 124, the reservoir is filled 126 with liquid cryogen to a desired level and dosing can resume.

Controller 50 is connected to a user interface (not shown) that allows the operator to set such parameters as dose duration and valve stem stroke, and to turn the dosing on and off. Controller 50 also receives inputs from various sensors, such as level sensor 14, pressure sensors 52 and 54, and various temperature sensors. For control of the electromagnetic actuator 40, controller 50 also receives a signal indicating a presence of a container to be dosed, such as a single pulse from a container sensor (not shown), and a signal from an encoder embedded in the electromagnetic actuator that is responsive to valve stem displacement. There may be, for example, 300 to 1500 encoder pulses per container dosing cycle. Controller 50 also has outputs for controlling the various valves, such as inlet valve 4, purge gas valve 34, back pressure valve 46, exit valve 56 and vent valve 64.

Figure 2:
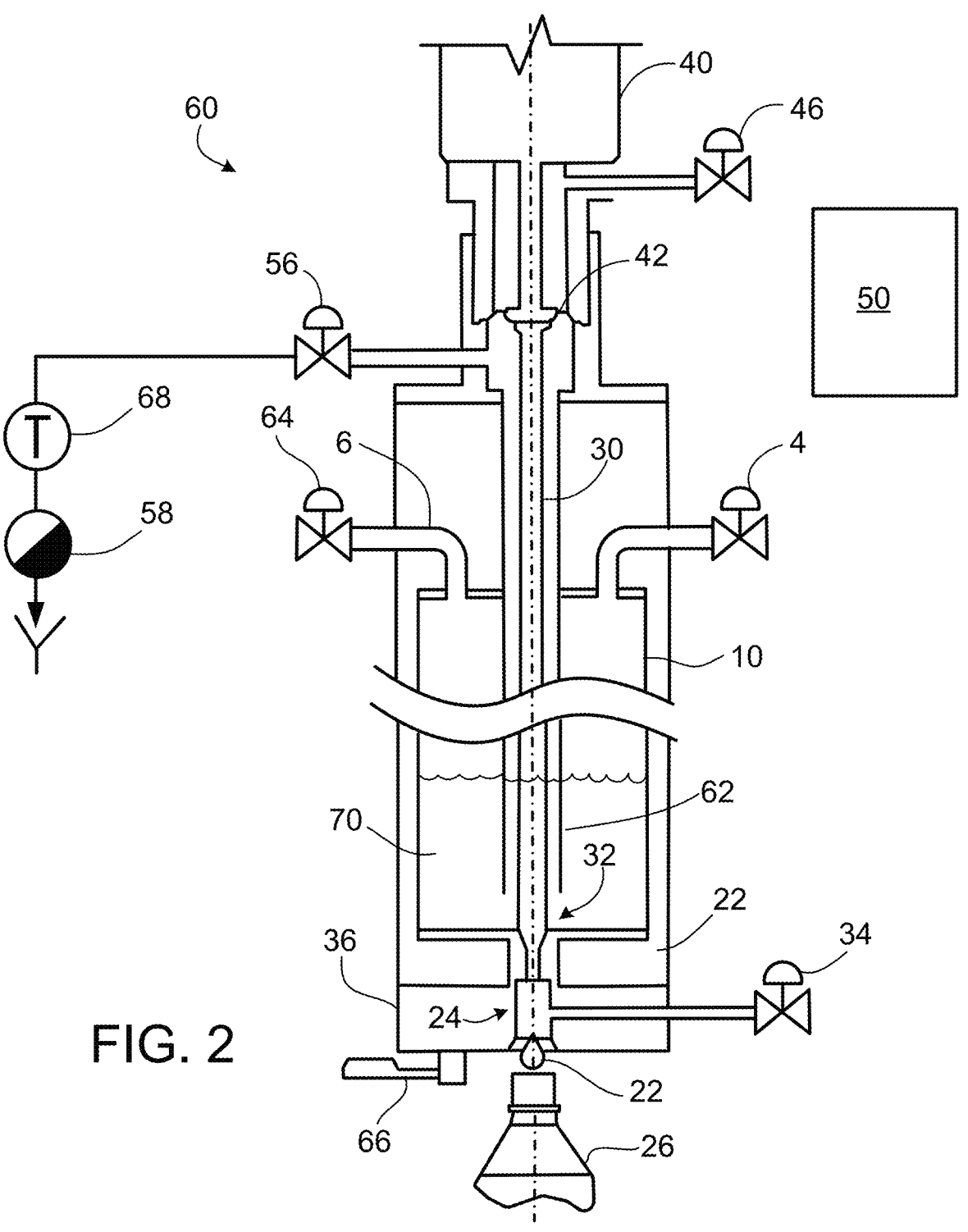
FIG. 2 is a schematic diagram of a second embodiment of a liquid cryogen delivery system for controlled dosing of liquid cryogen.

Referring to FIG. 2, aseptic liquid cryogen dosing head 60 is similar in function to the system shown in FIG. 1, but the cryogen reservoir is concentric about the valve stem 30, which extends from diaphragm 42 into the reservoir surrounded by a tube 62 that extends to below the free surface of the liquid cryogen 70 in the reservoir. In this example, the reservoir vent valve 64 is shown. As in the example of FIG. 1, all of the valves are controlled by controller 50 to perform the diaphragm and leakage tests discussed above, as well as a sterilization of the aseptic space and surfaces. This example also shows a shutter 66 controlled to pivot to cover the dosing outlet during sterilization and when the system is not in use. The shutter defines a small hole through which condensate can drip out of the dosing outlet cavity during sterilization. Some system components, such as a level switch or sensor coupled to fill valve 4, and various pressure and temperature sensors (other than a temperature sensor 68 in the steam vent line) are not shown, for clarity.

While a number of examples have been described for illustration purposes, the foregoing description is not intended to limit the scope of the invention, which is defined by the scope of the appended claims. There are and will be other examples and modifications within the scope of the following claims. For example, while a fixed-edge diaphragm is described as the seal along the dosing valve stem, a sliding seal (such as an O-ring or lip seal sliding along the stem surface) can be employed, although extra precaution should be taken to ensure that the entirety of the valve stem surface that is exposed to the aseptic cavity in use is properly sterilized.

What is claimed is:

1. An aseptic liquid cryogen dosing head, comprising
a liquid cryogen reservoir in communication with a dosing outlet;
an actuator operable to open and close the dosing outlet;
a seal separating the liquid cryogen reservoir from a cavity between the seal and the actuator, the seal providing an air-tight seal during operation; and
a controller operable to perform a head leakage test, including
pressurizing the cavity with a pressure higher than a pressure within the reservoir, to check for leakage past the seal; and
pressurizing the reservoir to check for leakage from the liquid cryogen reservoir.

2. The aseptic liquid cryogen dosing head of claim 1, wherein the controller is also operable to perform a sterilization cycle of the head, comprising introducing a pressurized sterilization fluid into the reservoir, while introducing a gas at a countering pressure into the cavity, thereby keeping the dosing outlet in a closed condition during sterilization.

3. The aseptic liquid cryogen dosing head of claim 2, wherein the pressurized sterilization fluid comprises steam.

4. The aseptic liquid cryogen dosing head of claim 2, wherein the controller is configured to perform the head leakage test both before and after performing the sterilization cycle.

5. The aseptic liquid cryogen dosing head of claim 1, wherein the seal comprises a diaphragm.

6. The aseptic liquid cryogen dosing head of claim 1, wherein the reservoir includes a tube extending from above a liquid cryogen level to below the liquid cryogen level.

7. The aseptic liquid cryogen dosing head of claim 1, wherein the reservoir comprises a liquid cryogen feed conduit filled with liquid cryogen in operation and extending from a primary cavity of the reservoir to the dosing outlet.

8. The aseptic liquid cryogen dosing head of claim 1, wherein the actuator comprises a servomotor.

9. The aseptic liquid cryogen dosing head of claim 1, wherein the actuator is controllable to alter a dosing valve stem displacement distance and duration.

10. The aseptic liquid cryogen dosing head of claim 1, wherein the actuator is controllable to alter a rest position of a dosing valve stem with respect to the dosing outlet.

11. The aseptic liquid cryogen dosing head of claim 1, further comprising a dosing outlet gas flow valve controllable to introduce a flow of sterile gas from a pressurized source to the dosing outlet to inhibit frost accumulation.

12. The aseptic liquid cryogen dosing head of claim 11, wherein the dosing outlet gas flow valve is controllable to open when the actuator is not operating to dispense a dose of liquid cryogen.

13. The aseptic liquid cryogen dosing head of claim 11, wherein the dosing outlet gas flow valve includes a fixed bypass orifice that allows a continuous flow of the sterile gas to the dosing outlet when the actuator is operating to dispense a dose of liquid cryogen.

14. The aseptic liquid cryogen dosing head of claim 11, wherein the dosing outlet gas flow valve is arranged to introduce the flow of the sterile gas to a portion of the dosing outlet open to atmospheric pressure.

15. A method of sterilizing a liquid cryogen dosing head, comprising
performing a system leakage test by pressurizing a first cavity between a dosing valve stem seal and an electromagnetic dosing actuator, as well as a second cavity on an opposite side of the dosing valve stem seal, to check for system leakage;

testing for leakage past the seal by reducing pressure in the second cavity and, with the second cavity pressure reduced, monitoring pressure in the first cavity over a predetermined time interval; and then in response to passing the seal leakage test, introducing a sterilization fluid to the second cavity and maintaining the sterilization fluid in the second cavity under conditions that cause sterilization of the second cavity.

\* \* \* \* \*